United States Patent
Speronello et al.

(10) Patent No.: US 6,432,322 B1
(45) Date of Patent: *Aug. 13, 2002

(54) MASSIVE BODIES FOR PRODUCING HIGHLY CONVERTED SOLUTIONS OF CHLORINE DIOXDE

(75) Inventors: Barry K. Speronello, Belle Mead; Gerald S. Koermer, Roseland; Appadurai Thangaraj, Edison; Ahmad Moini, Princeton, all of NJ (US)

(73) Assignee: Engelhard Corporation, Iselin, NJ (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/496,803

(22) Filed: Feb. 2, 2000

(51) Int. Cl.[7] .......................... C01B 11/10; C01B 11/02
(52) U.S. Cl. ............................ 252/187.23; 252/187.21
(58) Field of Search ...................... 252/187.23, 187.34, 252/186.21, 186.35, 187.21

(56) References Cited

U.S. PATENT DOCUMENTS

| 2,071,094 A | 2/1937 | Vincent ........................ 167/17 |
| 4,104,190 A | 8/1978 | Hartshorn ............... 252/187.23 |
| 4,547,381 A * | 10/1985 | Mason et al. ............... 426/316 |
| 4,689,169 A * | 8/1987 | Mason et al. ........... 252/186.24 |
| 5,324,447 A | 6/1994 | Lam et al. .............. 252/187.23 |
| 5,399,288 A | 3/1995 | Marzouk et al. ........ 252/187.23 |
| 5,719,100 A | 2/1998 | Zahradnik et al. ........... 502/417 |
| 6,007,735 A * | 12/1999 | Creed ..................... 252/186.25 |
| 6,197,215 B1 * | 3/2001 | Pitochelli ................ 252/187.21 |
| 6,238,643 B1 * | 5/2001 | Thangaraj et al. ........... 423/477 |
| 6,294,510 B1 * | 9/2001 | Norman et al. .............. 510/191 |

FOREIGN PATENT DOCUMENTS

| DE | 27 12 574 A | 10/1977 |
| EP | 581 550 A | 2/1994 |
| GB | 608068 | 9/1948 |
| WO | WO 99/24356 | 5/1999 |
| WO | WO 99/62817 | 12/1999 |

OTHER PUBLICATIONS

Patent Abstracts of Japan vol. 014, No. 227 (C–0718), May 15, 1990 (190–05–15) and Japan 01 055201 A (Herusu Kosan) Feb. 23, 1990.

* cited by examiner

Primary Examiner—Joseph D. Anthony
(74) Attorney, Agent, or Firm—Stephen I. Miller

(57) ABSTRACT

Massive bodies for rapidly and safely preparing highly converted solutions of chlorine dioxide are disclosed. These massive bodies when added to water produce more chlorine dioxide than when the equivalent weights of the ingredients in powder form are added to water. The solutions produced by the addition of massive bodies to water are also disclosed. The concentration of chlorine dioxide in the solution is such that the ratio of the concentration of chlorine dioxide to the sum of the concentrations of chlorine dioxide and chlorite anion is greater than 0.25:1 by weight.

12 Claims, No Drawings

MASSIVE BODIES FOR PRODUCING HIGHLY CONVERTED SOLUTIONS OF CHLORINE DIOXDE

BACKGROUND OF THE INVENTION

Free molecular chlorine dioxide in solution is an effective agent for the control of microorganisms and biological film deposits. However, the most common way to produce such solutions of free chlorine dioxide is to use an expensive and complicated chemical generator (see for example U.S. Pat. No. 5,009,875).

British patent 608,068 teaches the use of organic acid anhydrides to convert chlorite anion to free chlorine dioxide at a generally neutral pH. The fire and explosion dangers that result from combining a strong oxidizing chemical, such as sodium chlorite, with an organic chemical are also well known. As a result of the low conversion ratio produced by the compositions of this British patent, and the dangers inherent in compositions combining sodium chlorite and organic chemicals, the compositions of this British patent have received little commercial interest.

Recently, a membrane type device containing powdered chlorine dioxide precursor chemicals that produces a solution of free molecular chlorine dioxide when the device is immersed in water was described, see WO 99/24356. While this membrane device is superior to the prior art methods of producing chlorine dioxide solutions, the device has some shortcomings. It is relatively expensive (due to the cost of the membrane and of assembly), and the rate of chlorine dioxide delivery can be too slow for certain applications. Also, the device may float on the surface of the water/solution (due to entrapped air or chlorine dioxide gas), and this can result in the loss of some chlorine dioxide to the gas phase. Finally, the preferred membranes are insoluble in water, and may need to be removed from the chlorine dioxide solution after the chlorine dioxide generating reactions are completed. Removal of the spent membrane from the chlorine dioxide solution may, at times, be considered inconvenient.

The prior art also describes attempts to produce chlorine dioxide solutions from solid mixtures, including solid compacts such as tablets and briquettes, which are comprised, of materials that will generate chlorine dioxide gas when contacted with liquid water.

U.S. Pat No. 2,071,094 discloses dry solid compositions, including briquettes, comprised of a soluble chlorite and an acidifying agent which when contacted with water produce a "deodorizing reaction" as the dry composition begins to dissolve (see col. 1, lines 34–38 and col. 2, lines 24–27). Upon reading this patent, it is not clear what is produced when the composition comes into contact with water. The substance, chlorine dioxide, is never mentioned and the only time the word "solution" is used it is with reference to an aqueous solution of sodium chlorite (see col. 1, line 58). Thus, it cannot be ascertained whether the inventor was attempting to, or indeed ever did obtain an aqueous solution of chlorine dioxide when his briquette was contacted with water.

U.S. Pat. No. 5,324,447 describes, inter alia, a tablet comprising a chlorine dioxide precursor (e.g., sodium chlorite) and an activator component (e.g., an organic acid anhydride) which are present in amounts effective to produce (contact) lens disinfecting amounts of chlorine dioxide in a liquid medium (see, col. 3, lines 10–16). The term disinfecting amount is defined as such amount as will reduce the microbial burden by one log order preferably in ten (10) minutes or less (see col. 4, lines 11–15). This amount represents very little free chlorine dioxide, as even as little as 2 ppm of free chlorine dioxide can result in a 6 log bacterial reduction in 15 minutes. The patent does not disclose the amount of chlorine dioxide that is generated when a tablet of the invention is dissolved in water. Thus, all of the examples utilize aqueous solutions of stabilized chlorine dioxide and not water to test the tablets.

U.S. Pat. No. 5,399,288 discloses a solid composition releasing chlorine dioxide immediately after dissolution in water (see col. 1, lines 5–7). The composition comprises a chlorite salt, an oxidizing chlorine releasing agent and a proton donor present in the ratio of 4:1:3 (see col. 1, lines 65–67). When the oxidizing chlorine-releasing agent is omitted from the composition, the final yield of chlorine dioxide obtained was 63% but after three days (see Example 5). Further, and importantly, this patent does not discuss the preparation of tablets (see col. 2, lines 19–21). Thus, it appears that only powdered mixtures of reactants are disclosed.

U.S. Pat. No. 5,719,100 discloses production of chlorine dioxide in an aqueous solution from a tablet comprising a composition of sodium chlorite and an acid activator wherein the composition requires a reaction-preventing barrier between the sodium chlorite, [i.e., a protective reactive coat is formed on the sodium chlorite before it is mixed with the acid activator (see col. 4, lines 61–63) and the acid activator such that the two active ingredients do not "explosively react" together prematurely (see col. 4, line 53), i.e., a stable composition is obtained (see col. 4, line 46 through col. 5, line 9).

The present invention provides an improved device in the form of a massive body for the production of chlorine dioxide solutions. This new device rapidly provides high yield solutions of chlorine dioxide and overcomes shortcomings of prior art solid compositions for producing such solutions.

DESCRIPTION OF THE INVENTION

This invention provides a massive body that rapidly produces a solution of chlorine dioxide when immersed in water. The invention also includes the solutions obtained when a massive body is immersed in water. As used herein the term "massive body" means a solid shape, preferably a porous solid shape, comprising a mixture of granular particulate ingredients wherein the size of the particles comprising the ingredients is substantially smaller than the size of the massive body. Such massive bodies may be formed by a variety of means known in the art, such as tabletting, briqueting, extrusion, sintering, granulating and the like. The preferred method of forming such massive bodies is by compression, also known as tabletting. For reasons of convenience, hereinafter references to tablets and tabletting shall be understood to be representative of massive bodies made by any method.

The tablet is comprised of a source of chlorite anions such as an alkali or alkaline earth metal chlorite, preferably sodium chlorite and one or more dry solid acid sources. Examples of such dry solid acid sources include inorganic acid salts, such as sodium acid sulfate, potassium acid sulfate, sodium dihydrogen phosphate, and potassium dihydrogen phosphate; salts comprising the anions of strong acids and cations of weak bases, such as aluminum chloride, aluminum nitrate, cerium nitrate, and iron sulfate; solid acids that can liberate protons into solution when contacted with water, for example a mixture of the acid ion exchanged form of molecular sieve ETS-10 (see U.S. Pat. No. 4,853, 202) and sodium chloride; organic acids, such as citric acid and tartaric acid; and mixtures thereof. Preferably the solid acid source is a solid inorganic acid source, and most preferably is sodium bisulfate. Surprisingly, a very high conversion rate of the chlorite anion to chlorine dioxide is obtained by use of the tablets of the invention. Thus, when the equivalent weights of tablet ingredients in powdered form are added to the same volume of water as the corresponding tablet, a much larger amount of chlorine dioxide is produced by the tablet than from the powder. Reasonable variations in stirring rate and/or water temperature have little to no effect on this surprising phenomenon. Thus, the tablets of the invention have been observed rapidly to produce a highly converted solution of free molecular chlorine dioxide, meaning that the conversion ratio (chlorite anion to chlorine dioxide) is >0.25. The term, conversion ratio, when utilized herein means the calculated ratio of the free chlorine dioxide concentration in the product solution to the sum of free chlorine dioxide plus non-reacted chlorite ion concentrations in the product solution. Further, the chlorine dioxide solution is rapidly produced in a safe and controlled manner; and when the chlorine dioxide concentration so produced is at typical use levels (0.5–200 ppm by weight) in typical tap water, the solution will contain substantially no free chlorine or hypochlorite anion and will have a generally neutral pH (i.e., pH 5–9). By the term, rapidly produced, we mean that total chlorine dioxide production is obtained in less than about 8 hours, preferably in less than about 2 hours and most preferably in less than about 1 hour.

The tablets of the present invention may, if desired, contain optional additional ingredients, which may be useful, for example to assist in the tabletting process, to improve the physical or aesthetic characteristics of the produced tablets and to assist tablet solubilization and/or the yield of chlorine dioxide obtained. Such ingredients include but are not limited to fillers such as attapulgite clay and sodium chloride; tabletting and tablet die lubricants; stabilizers; dyes; anti-caking agents; desiccating filling agents such as calcium chloride and magnesium chloride; pore forming agents such as a swelling inorganic clay, e.g., Laponite clay available from Southern Clay Products, Inc.; a chlorine producing agent such as dichlorocyanuric acid and salts thereof such as the sodium salt (NaDCC); and a framework former that can react with one or more other constituents in the formulation to produce a low solubility porous framework structure in which the chlorine dioxide forming reactions may proceed. Effervescing agents such as sodium bicarbonate may be included in small amounts, but they can reduce the conversion of chlorite anion to chlorine dioxide by accelerating breakup and dissolution of the tablet.

In general the tablets of the invention are superior to the prior art membrane device, see e.g., WO 99/24356, for the following reasons:

Tablets are typically less costly than the membrane device because they can be manufactured at a high rate on commercially available equipment and do not require the expense of a membrane enclosure to function;

Tablets generally produce chlorine dioxide at a higher rate than membrane devices, since the tablet does not have a membrane to restrict the escape of chlorine dioxide into solution;

The membrane devices frequently float when they are added to water while the tablets of the invention sink in water so they lose little chlorine dioxide to the gas phase; and In one preferred mode, the tablet of the invention is completely soluble in water so the need to remove residue from the product chlorine dioxide solution is avoided.

While not wishing to be bound by any theory of operation, we believe that the enhanced yield of chlorine dioxide which is obtained by the use of the tablets of the invention may be explained in the following way. The tablet device functions when water enters the pore space within a tablet and produces a concentrated, acidic solution of chlorite anion within the pore space. The acid and chlorite (and optional ingredients that may be present) react under these concentrated conditions in the pores of the tablet rapidly to produce chlorine dioxide which diffuses out of the tablet into the bulk solution.

For the tablets to function properly, it is believed important that the chemical reactions occur in concentrated solution within the pore structure. There is little or no chlorine dioxide formed when the equivalent tablet ingredients in powder form are rapidly dissolved in aqueous media.

The invention includes two general types of tablet devices. One type of device comprises tablets that are fully soluble in water, and the preferred formulation of such tablets comprises dried powdered technical grade sodium chlorite and a dried powdered acid source, preferably sodium bisulfate. Additional dried powdered ingredients such as magnesium chloride and NaDCCA may optionally be added to even further improve the yield and rate of production of the chlorine dioxide. The dried powdered ingredients are mixed and the resultant powdered mixture is compressed in a tablet die at a pressure sufficient to produce a substantially intact tablet, typically about 1000–10,000 lb/in$^2$. The resultant tablets are stable during storage as long as they are protected from exposure to water (either liquid or vapor). The tablets rapidly produce a highly converted solution of free chlorine dioxide when immersed in water.

The second type of device comprises tablets, which are not fully soluble in water at a high rate. They are designed to have (or produce) a low solubility or slowly soluble porous framework structure in which the chlorine dioxide forming reactions may proceed to substantial completion prior to dissolution of the porous framework. Generally tablets of this second type convert a greater proportion of their chlorite anion precursor chemical to chlorine dioxide compared to the fully soluble tablets described above.

The preferred formulation for this second type of tablet device comprises dried powdered technical grade sodium chlorite, dried powdered sodium bisulfate and dried powdered calcium chloride. A dried powdered clay such as Laponite clay and dried powdered NaDCCA may optionally be added to even further improve the yield and rate of production of the chlorine dioxide. As with tablets of the first type, the dried powdered ingredients are mixed and the resultant powdered mixture is compressed in a tablet die at a pressure sufficient to produce a substantially intact tablet, typically about 1000–10,000 lb/in$^2$. The resultant tablets are stable during storage as long as they are protected from exposure to water (either liquid or vapor). They rapidly produce a highly converted solution of free chlorine dioxide when immersed in water.

Tablets of this second type generally provide more efficient conversion of chlorite anion to chlorine dioxide compared to tablets of the first type. It is believed that this occurs because the low solubility porous framework provides a favorable environment for the chlorine dioxide forming reactions to proceed until substantial exhaustion of the reactants.

Chlorine dioxide formation in tablets of the second type of device is believed to occur substantially within the favorable environment of the pore space of the low solubility (or slowly soluble) porous framework. Since the favorable pore structure of this framework appears to remain substantially intact during this reaction time, substantially all of the chlorite anion has an opportunity to react and form chlorine dioxide under favorable conditions within the pores. This maximizes chlorite conversion to chlorine dioxide. In contrast, a device of the first type is being dissolved into the bulk solution at the same time that it is producing chlorine dioxide. Since it is believed that the reagents will only react at a practically useful rate under concentrated conditions (such as those that exist within the pores of the tablets), that fraction of the chlorite that dissolves into bulk solution prior to conversion to chlorine dioxide will substantially remain as chlorite and not be converted to chlorine dioxide under the generally dilute conditions of the bulk solution.

The low solubility porous framework of the preferred composition of the second type of tablet device comprises a low solubility salt such as calcium sulfate and may additionally include a clay such as Laponite clay. The calcium sulfate preferably is formed from the reaction between calcium cations e.g., from the calcium chloride constituent and sulfate anions derived from the sodium bisulfate constituent. Other sources of calcium cations such as calcium nitrate as well as other sources of sulfate anions such as magnesium sulfate may also be used. The preferred clay, Laponite clay, is insoluble as provided and it is a swelling clay which, we believe, enhances the pore structure of the porous framework by forming cracks and cavities as it swells. We have found that forming the calcium sulfate framework in-situ via chemical reaction is particularly advantageous and that chlorine dioxide yield from such tablets is significantly better (nominally 25% better) compared to tablets in which calcium sulfate is a constituent of the initial powder formulation. The presence of the clay in addition to the calcium sulfate provides only a small improvement over the use of calcium sulfate without the clay.

By low solubility or slowly soluble porous framework, we mean a porous solid structure, which remains substantially undissolved in the product solution during the period of chlorine dioxide production. It is not necessary that the porous framework remain wholly intact during the reaction time to form chlorine dioxide. One aspect of this invention includes tablets of the second type in which the tablet disintegrates into substantially insoluble (or slowly soluble) granules that release chlorine dioxide into solution. This is acceptable, we believe, because the size of the granules is still large relative to the size of the pores within the pore space of the granules, so the necessary concentrated reaction conditions exist within the pore space despite the breakdown of the framework into granules.

In tablet devices of both types, it is preferred that the powdered ingredients be dry prior to mixing and tabletting in order to minimize premature chemical interaction among the tablet ingredients. When utilized herein the term dry means that each ingredient typically contains less than about 1% $H_2O$.

General Procedures for Making and Testing the Tablets of the Invention Tablet Formation The individual chemical components of the tablet formulation are dried prior to use. The desired amount of each component is carefully weighed into a plastic vial. In the following examples, formulations are given on a weight percent basis. The vial containing all the components of the tablet formulation is shaken to mix the components thoroughly. The contents of the vial are emptied into an appropriately sized die (e.g., 13-mm diameter for 1 g tablet). The plunger is placed in the die and the contents are pressed into a pellet using a hydraulic laboratory press. The maximum force reading on the press gauge was 2000 pounds unless otherwise noted. This pressure on the tablet punch may be converted to pounds/$in^2$ if the area of the face of the plunger in $in^2$ is known (typically 0.206 $in^2$ for a 1 g tablet). The resulting tablet is removed from the die and placed in a closed plastic vial until use (typically within 10 minutes).

Tablet Performance

The tablet is placed in a volumetric flask or container filled with a known amount of tap water. Chlorine dioxide evolution starts immediately as evidenced by bubbles and the appearance of a yellow color. The tablet is allowed to react until completion. Completion of the reaction depends, in part, on the tablet type and size. Typically the reaction time is 2 hours or less if a 1 g tablet is partially insoluble and 0.5 hr. if a 1 g tablet is completely soluble. When reaction is complete, the flask/container is shaken or stirred in order to mix the contents. Then the contents are analyzed. Typically, chlorine dioxide is measured by uv-vis spectrometry, using four wavelengths (the average value is reported). Chlorite and chlorine are measured by titration of typically 25 ml of chlorine dioxide solution using procedures equivalent to those found in the text, *Standard Methods for the Examination of Water and Wastewater*, $19^{th}$ Edition (1995) pages 4–57 and 4–58. This text is published jointly by the American Public Health Association, The American Water Works Association and the Water Environment Federation. The publication office is American Public Health Association, Washington, D.C. 20005. Total oxidants are measured by titration using a Brinkmann Autotitration System, 716 DMS Titrino equipped with a massive platinum electrode (Brinkmann Part No. 6.0415.100). The method is an iodimetric titration in an acid medium based on the oxidation of iodide to iodine and its subsequent reaction with the titrant, sodium thiosulfate. The typical procedure was as follows. One hundred milliliters of chlorine dioxide solution and a stirring bar were placed in a beaker and 2 g of potassium iodide (Reagent Crystals) and 10 ml of a 1N solution of sulfuric acid (Mallinckrodt) were added with stirring. The resulting solution is titrated with 0.1N thiosulfate solution (Aldrich Chemical Co.). The endpoint is automatically determined by the Brinkmann Titrino software. This endpoint is used to calculate the concentration of total oxidants in the sample. The pH of the original chlorine dioxide solution is measured using a pH electrode either on the solution "as is" and/or diluted with sufficient water to give approximately a 10 ppm concentration of chlorine dioxide.

Results

In the examples below, the above procedures are followed unless otherwise specified. Formulations are given as weight percents of each component on a dry basis. Technical grade sodium chlorite was used. Typically the actual sodium chlorite content of technical grade sodium chlorite is approximately 80% and the remainder is approximately sodium chloride (8.5%), sodium carbonate (6.1%) and sodium sulfate (4.5%). Yields are calculated on two bases. The first is the wt % yield of chlorine dioxide based on the tablet weight, i.e., wt % yield=100×(wt ClO2/wt tablet). The second is the chemical yield based on sodium chlorite. In this case one must take into account that technical grade sodium chlorite is only 80% pure. Thus, chemical % yield=

100×(moles ClO2 produced)/(moles of NaClO2 in tablet). The stoichiometry of the acid reaction of sodium chlorite to chlorine dioxide limits the yield to 80%.

Conversion ratio is calculated as (wt chlorine dioxide)/(wt chlorine dioxide+wt chlorite). If the chlorite content of the solution was not determined or is unknown, a "minimum conversion ratio" is calculated. This ratio is wtClO2/wt total oxidant. Total oxidant typically consists entirely of chlorine dioxide, chlorite and chlorine. The chlorine content of solutions from tablets is typically low, so this minimum conversion ratio is a reasonable approximation of the conversion ratio. Examples are illustrated below.

EXAMPLE 1

Three one-gram tablets were made with the following composition:

| | |
|---|---|
| Sodium Chlorite | 38% |
| Dichloroisocyanuric acid, sodium salt | 9 |
| Sodium Bisulfate | 35 |
| Calcium Chloride | 18 |

The tablets were made at 3000 lb. pressure. Each tablet was placed in three liters of tap water for two hours with the following results.

| | A | B | C |
|---|---|---|---|
| ClO2 ppm | 47.5 | 46.9 | 47.0 |
| Total Oxidant (ppm) | 58.7 | 58.0 | 53.2 |
| PH | 6.8 | 6.8 | 6.8 |
| Wt % Yield | 14.3 | 14.1 | 14.1 |
| Chemical % Yield | 63 | 62 | 62 |
| Conversion Ratio* | 0.81 | 0.81 | 0.88 |

*Minimum ratio; ppm ClO2/ppm total oxidant

EXAMPLE 2

A one-gram tablet was made with the following composition:

| | |
|---|---|
| Sodium Chlorite | 37% |
| Dichloroisocyanuric acid, sodium salt | 15 |
| Sodium Bisulfate | 30 |
| Calcium Chloride | 18 |

The tablet was made at 2000 lb. pressure. The tablet was placed in three liters of tap water for 2.5 hours with the following results.

| | |
|---|---|
| ClO2 ppm | 49.8 |
| Total Oxidant ppm | 69.7 |
| PH | 6.6 |
| Wt % Yield | 14.9 |
| Chemical % Yield | 68 |
| Conversion ratio* | 0.71 |

*Minimum ratio; ppm ClO2/ppm total oxidant

EXAMPLE 3

Two one-gram tablets were made with the following composition:

| | |
|---|---|
| Sodium Chlorite | 7% |
| Dichloroisocyanuric acid, sodium salt | 1 |
| Sodium Bisulfate | 12 |
| Calcium Chloride | 48 |
| Sodium Chloride | 16 |
| Sodium Sulfate | 16 |

The tablets were made at 2000 lb. pressure. Each tablet was placed in 0.5 liters of tap water for 1 hour with the following results.

| | A | B |
|---|---|---|
| ClO2 ppm | 57.4 | 58.0 |
| Chlorite ppm | 4.3 | 6.1 |
| Chlorine ppm | 2.2 | 2.2 |
| pH (10 ppm) | 6.76 | 6.77 |
| Wt % Yield | 2.87 | 2.90 |
| Chemical % Yield | 69 | 69 |
| Conversion ratio | 0.93 | 0.90 |

EXAMPLE 4

Two one-gram tablets were made with the following composition:

| | |
|---|---|
| Sodium Chlorite | 7% |
| Dichloroisocyanuric acid, sodium salt | 1 |
| Sodium Bisulfate | 12 |
| Sodium Chloride | 40 |
| Magnesium Chloride | 40 |

The tablets were made at 2000 lb. pressure. Each tablet was placed in 0.5 liter of tap water for 0.5 hour with the following results.

| | A | B |
|---|---|---|
| ClO2 ppm | 53.0 | 54.8 |
| Chlorite ppm | 7.6 | 4.1 |
| Chlorine ppm | 0.1 | 1.2 |
| pH (10 ppm) | 7.41 | 7.36 |
| Wt % Yield | 2.65 | 2.74 |
| Chemical % Yield | 63 | 66 |
| Conversion ratio | 0.87 | 0.93 |

EXAMPLE 5

Two one-gram tablets were made with the following composition:

| | |
|---|---|
| Sodium Chlorite | 26% |
| Dichloroisocyanuric acid, sodium salt | 7 |
| Sodium Bisulfate | 26 |
| Sodium Chloride | 20 |
| Magnesium Chloride | 21 |

The tablets were made at 2000 lb. pressure. Each tablet was placed in 1.0 liter of tap water for 0.25 hour with the following results.

|  | A | B |
|---|---|---|
| ClO2 ppm | 104.2 | 105.1 |
| Total Oxidant ppm | 115.3 | 109.7 |
| pH | 6.47 | 6.52 |
| Wt % Yield | 10.42 | 10.51 |
| Chemical % Yield | 67 | 68 |
| Conversion ratio* | 0.90 | 0.96 |

*Minimum ratio; ppm ClO2/ppm total oxidant

EXAMPLE 6

A one-gram tablet was made with the following composition:

| | |
|---|---|
| Sodium Chlorite | 34% |
| Dichloroisocyanuric acid, sodium salt | 8 |
| Sodium Bisulfate | 26 |
| Sodium Chloride | 16 |
| Magnesium Chloride | 16 |

The tablet was made at 2000 lb. pressure. The tablet was placed in 1.0 liter of tap water for 0.25 hour with the following results

| | |
|---|---|
| ClO2 ppm | 123.3 |
| Total Oxidant ppm | 144.4 |
| pH | 6.47 |
| Wt % Yield | 12.3 |
| Chemical % Yield | 61 |
| Conversion ratio* | 0.85 |

*Minimum ratio; ppm ClO2/ppm total oxidant

EXAMPLE 7

This example illustrates the efficacy of generating chlorine dioxide by using a tablet as opposed to powder. Two one-gram samples of the following formulation were prepared.

| | |
|---|---|
| Sodium Chlorite | 25% |
| Sodium Dichloroisocyanurate | 8 |
| Sodium Bisulfate | 31 |
| Calcium Chloride | 31 |
| Laponite | 5 |

One sample was left as a mixed powder. The other sample was pressed into a tablet using 2000 pounds pressure. Each sample was placed in ten liters of water that was stirred using a paddle stirrer. The results after 1.5 hours indicate that the yield of chlorine dioxide from the tablet is an order of magnitude greater than from the equivalent powder.

|  | Tablet | Powder |
|---|---|---|
| ClO2 ppm | 8.8 | 0.75 |
| Total Oxidant ppm | 12.0 | 14.5 |
| pH | 7.20 | 7.18 |
| Wt % Yield | 8.8 | 0.8 |
| Chemical % Yield | 59 | 5 |
| Conversion ratio* | 0.73 | 0.05 |

*Minimum ratio; ppm ClO2/ppm total oxidant

EXPERIMENT 8

This experiment shows that it is better to form calcium chloride in-situ in the tablet than to add calcium sulfate to the tablet formulation.

The following formulations were made into tablets using 6000 lb. pressure. The tablets were placed into 1 liter of tap water. After 3 hours the resulting solutions were analyzed.

|  | A | B |
|---|---|---|
| Sodium Chlorite (T) (g) | 0.30 | 0.30 |
| Sodium Dichloroisocyanurate (g) | 0.10 | 0.10 |
| Sodium Bisulfate (g) | 0.30 | 0.30 |
| Calcium Chloride (g) | 0.25 | |
| Calcium Sulfate (g) | | 0.25 |
| Laponite (g) | 0.05 | 0.05 |
| Total (g) | 1.00 | 1.00 |

Results

|  | A | B |
|---|---|---|
| ClO2 ppm | 124.0 | 96.0 |
| Total Oxidant ppm | 133.0 | 120.3 |
| pH | 6.7 | 6.2 |
| Wt % Yield | 12.4 | 9.6 |
| Chemical % Yield | 69 | 54 |
| Conversion ratio* | 0.93 | 0.80 |

*Minimum ratio: ppm ClO2/ppm total oxidant

EXAMPLE 9

A one-gram tablet was prepared from the following formulation using 6000 lb. pressure:

0.167 g Sodium Chlorite Technical 0.500 g Sodium Bisulfate 0.330 g Sodium Chloride The tablet was placed in 1 liter of tap water and analyzed after 10 minutes (all components soluble).

Results

| | |
|---|---|
| ClO2 ppm | 40 |
| Total Oxidant ppm | 48.6 |
| pH | 3.6 |
| Wt % Yield | 4 |
| Chemical % Yield | 40 |
| Conversion ratio* | 82 |

*Minimum ratio; ppm ClO2/ppm total oxidant

EXAMPLE 10

Three tablets of varying size were prepared from a single formulation as shown below. The tablets were placed in enough tap water so the final concentration of chlorine dioxide would be 100–200 ppm. Since larger tablets take more time to release chlorine dioxide, the reaction time was adjusted (as shown) to insure that sampling occurred when reaction was complete. Different dies were used to press the tablets such that the height/diameter ratios for the tablets were substantially equivalent and the pressure used to press the tablets were approximately the same on a force/unit cross sectional area basis.

|  | A | B | C |
|---|---|---|---|
| NaClO2 (T) (g) | 0.38 | 4.22 | 34.2 |
| Na Dichloroisocyanurate (g) | 0.09 | 1.00 | 8.10 |
| Sodium Bisulfate (g) | 0.35 | 3.89 | 31.5 |
| Calcium Chloride (g) | 0.18 | 2.00 | 16.2 |
| Total (g) | 1.00 | 11.11 | 90.0 |
| Tablet Pressure (lb.) | 2000 | 6000 | 20000 |
| Volume (Liters) | 1 | 10 | 120 |
| Reaction Time (h) | 1.0 | 2.0 | 7.0 |

Results are shown below

|  | A | B | C |
|---|---|---|---|
| ClO2 ppm | 139.8 | 161.9 | 103.2 |
| Total Oxidant ppm | 159.0 | 169.1 |  |
| Chlorite ppm |  |  | 15.93 |
| Chlorine ppm |  |  | 5.34 |
| pH (@ 10 ppm) | 6.7 | 7.1 | 7.3 |
| Wt % Yield | 14.0 | 14.6 | 13.8 |
| Chemical % Yield | 62 | 64 | 61 |
| Conversion ratio | 88* | 96* | 87 |

*Minimum ratio; ppm ClO2/ppm total oxidant

EXAMPLE 11

Three tablets of varying size were prepared from a single formulation as shown below. The tablets were placed in enough tap water so the final concentration of chlorine dioxide would be 100–200 ppm. Since larger tablets take more time to release chlorine dioxide, the reaction time was adjusted (as shown). Sampling occurred when reaction was complete, i.e. after the tablet dissolved. Different dies were used to press the tablets such that the height/diameter ratios for the tablets were substantially equivalent and the pressure used to press the tablets were approximately the same on a force/unit cross sectional area basis.

|  | A | B | C |
|---|---|---|---|
| NaClO2 (T) (g) | 0.26 | 2.886 | 23.14 |
| Na Dichloroisocyanurate (g) | 0.07 | 0.777 | 6.23 |
| Sodium Bisulfate (g) | 0.26 | 2.886 | 23.14 |
| Magnesium Chloride (g) | 0.21 | 2.331 | 18.69 |
| Sodium Chloride (g) | 0.20 | 2.220 | 17.80 |
| Total (g) | 1.00 | 11.10 | 89.00 |
| Pressure (lb.) | 2000 | 6000 | 20000 |

|  | A | B | C |
|---|---|---|---|
| Volume (L) | 1 | 10 | 121.4 |
| Reaction Time (h) | 0.25 | 0.5 | 1.0 |

The results are shown below

|  | A | B | C |
|---|---|---|---|
| ClO2 ppm | 97.9 | 111.1 | 64.7 |
| Total Oxidant ppm | 120.6 | 132.8 | 86.5 |
| pH | 7.6 | 7.7 | 7.0 |
| Wt % Yield | 9.8 | 10.0 | 8.8 |
| Chemical % Yield | 63 | 65 | 57 |
| Conversion ratio* | 0.81 | 0.84 | 0.75 |

*Minimum ratio; ppm ClO2/ppm total oxidant

EXAMPLE 12

Various solids were added to the tablet formulation to determine if there was benefit from having these insoluble solids in the tablet. Tablet pressure was 6000 lb. unless noted. Reaction times were generally as long as the tablet still bubbled (released gas). The generic formulation for the tablets is shown below:

| Sodium Chlorite (T) (g) | 0.1 |
|---|---|
| Sodium Chloride (g) | 0.2 |
| Sodium Bisulfate (g) | 0.3 |
| Additive (g) | 0.4 |
| Total (g) | 1.0 |

One-gram tablets were placed in 1 liter of tap water. Results are shown below

| Additive | Na Laponite | H+ Laponite | ETS-10 | Silica Gel |
|---|---|---|---|---|
| ClO2 ppm | 37.4 | 38.1 | 13.9 | 20.5 |
| Total Oxidant ppm | 46.5 | 49.3 | 16.2 | 22.5 |
| pH | 6.7 | 6.4 |  |  |
| Reaction Time |  |  | 0.25 |  |
| Wt % Yield | 3.7 | 3.8 | 1.6 | 2.1 |
| Chemical % Yield | 63 | 64 | 23 | 34 |
| Conversion Ratio* | 0.80 | 0.77 | 0.86 | 0.91 |

*Minimum ratio; ppm ClO2/ppm total oxidant

| Additive | LaY | Veegum | Bentone | Attagel 40 |
|---|---|---|---|---|
| ClO2 ppm | 18.1 | 20.1 | 29.9 | 25.1 |
| Total Oxidant ppm | 24.7 | 37.1 | 34.3 | 35.6 |
| pH |  | 6.3 | 6.3 |  |
| Reaction Time | 1 |  |  |  |
| Wt % Yield | 1.8 | 2.0 | 3.0 | 2.5 |
| Chemical % Yield | 30 | 34 | 50 | 42 |
| Conversion Ratio* | 0.73 | 0.54 | 0.87 | 0.70 |

*Minimum ratio: ppm ClO2/ppm total oxidant.

| Additive | Montmorillonite | Bentonite |
|---|---|---|
| ClO2 ppm | 12.5 | 6.5 |
| Total Oxidant ppm | 25.6 | 23.8 |
| pH | 6.1 | 5.9 |
| Reaction Time | | |
| Wt % Yield | 1.3 | 0.7 |
| Chemical % Yield | 21 | 11 |
| Conversion ratio* | 0.49 | 0.27 |

*Minimum ratio: ppm ClO2/ppm total oxidant

What is claimed:

1. A massive body comprising a metal chlorite and a solid acid source, said massive body containing no chlorine producing agent and being such that when added to liquid water the massive body will produce a solution of chlorine dioxide wherein the ratio of the concentration of chlorine dioxide to the sum of the concentrations of chlorine dioxide and chlorite anion is greater than 0.25:1 by weight.

2. The massive body defined in claim 1 wherein the metal chlorite is sodium chlorite.

3. The massive body defined in claim 1 which additionally comprises magnesium chloride.

4. The massive body defined in claim 1 which additionally comprises sodium chloride.

5. The massive body defined in claim 1 which is soluble in water.

6. The massive body defined in claim 5 which comprises sodium chlorite and sodium bisulfate.

7. The massive body defined in claim 1 which does not completely dissolve in water.

8. The massive body defined in claim 7 which comprises sodium chlorite and sodium bisulfate.

9. The massive body defined in claim 1 which additionally comprises a source of calcium cations.

10. The masssive body defined in claim 9 wherein the source of calcium cations is calcium chloride.

11. The massive body defined in claim 10 which additionally contains a swelling inorganic clay.

12. The massive body defined in claim 11 wherein the clay is Laponite clay.

* * * * *